US009360358B2

(12) United States Patent
Wang et al.

(10) Patent No.: US 9,360,358 B2
(45) Date of Patent: Jun. 7, 2016

(54) CORIOLIS MASS FLOW METER, VIBRATING TUBE DENSITY METER AND VIBRATING SHEET USED THEREIN

(75) Inventors: Fahui Wang, Qingdao (CN); Xinwang Cui, Qingdao (CN); Tingxu Zhang, Qingdao (CN); Junbao Wu, Qingdao (CN)

(73) Assignee: QINGDAO ADD VALUE FLOW METERING CO., LTD. (CN)

( * ) Notice: Subject to any disclaimer, the term of this patent is extended or adjusted under 35 U.S.C. 154(b) by 81 days.

(21) Appl. No.: 14/358,954

(22) PCT Filed: Mar. 8, 2012

(86) PCT No.: PCT/CN2012/000288
§ 371 (c)(1),
(2), (4) Date: Aug. 25, 2014

(87) PCT Pub. No.: WO2013/071680
PCT Pub. Date: May 23, 2013

(65) Prior Publication Data
US 2015/0033874 A1    Feb. 5, 2015

(30) Foreign Application Priority Data

Nov. 18, 2011    (CN) .......................... 2011 1 0367740

(51) Int. Cl.
*G01F 1/84*    (2006.01)
*G01N 9/00*    (2006.01)

(52) U.S. Cl.
CPC ............ *G01F 1/8422* (2013.01); *G01F 1/8409* (2013.01); *G01F 1/8413* (2013.01); *G01F 1/8477* (2013.01); *G01N 9/002* (2013.01)

(58) Field of Classification Search
CPC ........................................................ G01F 1/84
USPC ...................................... 73/861.355–861.357
See application file for complete search history.

(56) References Cited

U.S. PATENT DOCUMENTS 645,668 A    3/1900 Lemoon
4,491,025 A    1/1985 Smith
(Continued)

FOREIGN PATENT DOCUMENTS

CN    1100805 A    3/1995
CN    1127550 A    7/1996
(Continued)

OTHER PUBLICATIONS

Chinese Examination History of the corresponding priority application CN201110367740.5 with English translation attached, 16 pages.
(Continued)

*Primary Examiner* — Jewel V Thompson
(74) *Attorney, Agent, or Firm* — Cantor Colburn LLP

(57) ABSTRACT

The present invention relates to a Coriolis mass flow meter, a vibrating tube density meter and a vibrating sheet used therein, and more particularly, to a vibrating sheet for use in a Coriolis mass flow meter or a vibrating tube density meter, the vibrating sheet having at least one welded connecting portion that is fixedly welded to the flow tube of the Coriolis mass flow meter or the vibrating tube density meter, the flow tube being excited to vibrate around a revolving axis at the welded junction of the vibrating sheet and the flow tube. The welded connecting portions of the vibrating sheet are only formed in the stress insensitive region of the vibrating sheet, wherein the stress insensitive region is the region of the vibrating sheet which has an angle of not more than 45 degrees with respect to the revolving axis. In addition, the present invention also provides a Coriolis mass flow meter and a vibrating tube density meter using the vibrating sheet. The present invention not only simplifies the process, but also improves the measurement precision and service life of the Coriolis mass flow meter and the vibrating tube density meter.

12 Claims, 8 Drawing Sheets

(56) References Cited

U.S. PATENT DOCUMENTS

| | | | | |
|---|---|---|---|---|
| 8,302,489 | B2* | 11/2012 | Bell | G01F 1/74 73/861.04 |
| 8,573,067 | B2* | 11/2013 | Lanham | G01F 1/8418 73/861.355 |
| 8,596,142 | B2* | 12/2013 | Huber | G01F 1/8427 73/861.357 |
| 9,046,400 | B2* | 6/2015 | Henry | G01F 1/8404 702/45 |

FOREIGN PATENT DOCUMENTS

| CN | 101745721 A | 6/2010 |
|---|---|---|
| CN | 101837494 A | 9/2010 |
| CN | 101903538 A | 12/2010 |
| CN | 201765000 U | 3/2011 |
| CN | 102494726 A | 6/2012 |
| EP | 0685712 A1 | 12/1995 |
| JP | 10-185645 A | 7/1998 |
| WO | 95/03529 A1 | 2/1995 |
| WO | 00/57141 A1 | 9/2000 |

OTHER PUBLICATIONS

International Preliminary Report on Patentability for the international application No. PCT/CN2012/000288, dated May 20, 2014, 9 pages.
Written Opinion of the International Searching Authority for the international patent application No. PCT/CN2012/000288, dated Aug. 30, 2012, 8 pages.
English abstracts of related prior art references filed in an Information Disclosure Statement filed May 16, 2014, 5 pages.
International Search Report for International Application No. PCT/CN2012/000288, mailed Aug. 30, 2012 with English translation.

* cited by examiner

CORIOLIS MASS FLOW METER, VIBRATING TUBE DENSITY METER AND VIBRATING SHEET USED THEREIN

This is the U.S. national stage of application No. PCT/CN2012/000288, filed on 8 Mar. 2012. Priority under 35 U.S.C. §119(a) and 35 U.S.C. §365(b) is claimed from Chinese Application No. 201110367740.5, filed 18 Nov. 2011, the disclosure of which is also incorporated herein by reference.

TECHNICAL FIELD

The present invention relates to a Coriolis mass flow meter, a vibrating tube density meter and a vibrating sheet used therein.

BACKGROUND ART

A Coriolis mass flow meter is a meter for measuring liquid mass flow and other information (including, but not limited to, density, temperature, etc.) by means of Coriolis effect. Such a flow meter usually includes one or more straight or curved flow tubes. The liquid to be measured flows into the flow tube from one end thereof and out from the other end thereof. A commonly seen dual-flow-tube Coriolis mass flow meter 100 as shown in FIG. 1 is taken as an example, which structure is usually as follows: two flow tubes 111, 112 are parallel to each other and curved into U-shape; inlet ends of the flow tubes 111, 112 are fixed to an inlet manifold block 121, outlet ends of the flow tubes 111, 112 are fixed to an outlet manifold block 122, the inlet manifold block 121 is connected with an inlet flange 131, the outlet manifold block 122 is connected with an outlet flange 132, and there is usually a transverse tube 123 for support of and connection between opposing sides of the two manifold blocks 121 and 122; liquid to be measured flows into the inlet manifold block 121 through the inlet flange 131; the inlet manifold block 121 divides the liquid stream into two substantially equal liquid streams that flow into two flow tubes 111, 112 respectively; the separated liquid flows via the flow tubes 111, 112 into the outlet manifold block 122; the outlet manifold block 122 collects two liquid streams into one stream which flows via the outlet flange 132 into the conduit; a vibration exciter 141 is arranged in the middle portion of the flow tubes 111, 112, and a vibration sensor 142 is arranged at both sides of the vibration exciter 141 at a distance therefrom. The portion between the inlet flange 131 and the outlet flange 132 is a core sensing portion of the Coriolis mass flow meter. The portion of the flow tubes between two vibration sensors 142 is commonly named as a measuring section. The vibration sensors 142 are connected by cables with a signal processing device and a display device (not shown). The above all forms the Coriolis mass flow meter. The overall structure of other types, such as a single-flow-tube and a multi-flow-tube Coriolis mass flow meter, is also well-known to those skilled in the art and will not be described herein.

It is a disclosed technique that the Coriolis mass flow meter is used for measuring information of liquid, such as mass and density, which has been detailed in e.g. U.S. Pat. No. 4,491,025 published on Jan. 1, 1985. As known by those skilled in the art, the flow tube of the Coriolis mass flow meter vibrates in an inherent mode when in operation, thereby generating a corresponding resonance frequency. This resonance frequency is directly associated with flow tubes and the liquid therein. When being excited, the flow tubes will vibrate at a substantially fixed frequency. When there is no liquid in the flow tube or the liquid therein does not flow, the phases at the various points of the flow tube are the same (the phase mentioned herein means that the flow tube vibrates substantially in a path of sine signals, which is indicated by the formula $f(t)=A\sin(\omega t+\phi)$, wherein $\phi$ is the phase). When the liquid in the flow tube flows, a Coriolis acceleration is generated on the flow tube due to the presence of the Coriolis effect. This results in different phases at various points of the flow tube, wherein the phase at the inlet side lags behind that of the vibration exciter, and the phase at the outlet side exceeds that of the vibration exciter. Vibration sensors, which are respectively located at the inlet side and the outlet side with respect to the vibration exciter, measure the motion of the flow tubes. There is a particular relationship between the phase differences measured by the vibration sensors and the mass flow of the liquid flowing through the measuring section. The mass flow of the liquid can be measured by a phase difference of signals of the vibration sensors.

A vibrating tube density meter is substantially the same as the mass flow meter in terms of structure, and usually made of one or more straight or curved flow tubes fixed between the inlet manifold block and the outlet manifold block. The difference therebetween is that the vibrating tube density meter measures density in accordance with the relationship between the measured liquid density and the intrinsic frequency when the liquid passes through the flow tube, whereas the mass flow meter measures the mass flow of the liquid in accordance with the phase difference at different positions of the flow tube. The flow tube of the vibrating tube density meter vibrates in an inherent mode when in operation, thereby generating a corresponding resonance frequency. Change in density of the liquid in the flow tube leads to a variation of resonance frequency of the flow tube. The density of the liquid in the flow tube can be obtained by measuring the resonance frequency of the flow tube.

Generally speaking, the Coriolis mass flow meter and the vibrating tube density meter are fixed with vibrating sheets (also known as damping plates or bracing bars), each of which is disposed at a position with a certain distance from the inlet or outlet of the flow tubes, for instance, vibrating sheets 150 as shown in FIG. 1. Conventional vibrating sheets are usually thin flat sheets with through holes. For instance, in the dual-flow-tube Coriolis mass flow meter 100 as shown in FIG. 1, the prior art vibrating sheet 150 usually has two through holes, each of which has an entire circumference, and two flow tubes 111, 112 extend through the two through holes and are fixedly welded to the vibrating sheets 150 along the entire circumferences of the through holes by fusion welding or brazing. The desired vibrating mode of the Coriolis mass flow meter 100 when excited is that the two flow tubes 111, 112 move towards or apart from each other simultaneously, and then the phases of the movements of the two flow tubes are opposite to each other, which is called "out-of-phase" vibration, as shown by arrows A and A' in FIG. 2. The two flow tubes may also vibrate towards the same direction at the same time, which is called "in-phase" vibration, as shown by arrows B and B' in FIG. 3. When the flow tube is interfered by external vibration, the in-phase vibration and the out-of-phase vibration will be superposed together, which can influence the precision of flow measurement. One of the important reasons for superposition of the in-phase vibration and the out-of-phase vibration is that the in-phase vibration and the out-of-phase vibration have an identical revolving axis. When there is no vibrating sheet, the flow tube is directly fixed to the manifold blocks, and revolving axes of the in-phase vibration and the out-of-phase vibration are at a position near the junction of the flow tube and the manifold block. The in-phase vibration and the out-of-phase vibration have similar vibration frequencies. The more similar the frequencies are, the greater the interference with the out-of-phase vibration by the in-phase vibration. One way to avoid such case is to add a vibrating sheet at a position with a distance from the junction of the flow tube and the manifold block so as to connect the two flow tubes to each other. Then, the revolving axes N, N' of the in-phase vibration are adjacent to the junctions 115 of the flow tubes and the manifold blocks, and the revolving axes M, M' of the out-of-phase vibration are adjacent to the welded junctions 116 of the flow tubes and the vibrating sheets. The in-phase vibration and the out-of-phase vibration have not only different revolving axes but also different vibration frequencies. The in-phase vibration can hardly interfere with the out-of-phase vibration, which is good for accurately measuring desired data by the Coriolis mass flow meter and the vibrating tube density meter.

There are various types of vibrating sheets in the prior art. For instance, an international patent application No. WO95/03529 published on Feb. 2, 1995 describes several vibrating sheets as shown in FIGS. 4 to 6, wherein FIG. 4 shows a common type of vibrating sheet, and FIGS. 5 and 6 show two vibrating sheets aiming to reduce stress concentration as taught by the above-mentioned patent application. In the technical solution thereof, the flow tubes are fixed with the vibrating sheet by using a zinc-copper alloy to weld along the entire circumferences of the through holes after the two flow tubes pass through the corresponding through holes, as shown in FIG. 7.

The Chinese patent application No. CN101745721A published on Jun. 23, 2010 provides another type of vibrating sheet, as shown in FIG. 8, characterized in that a recess is disposed on the surface of the vibrating sheet around the through hole which the flow tube passes through, mainly for the purpose of facilitating manual argon arc welding. During fixing operation, the flow tube passes through a corresponding through hole, and then the flow tube and the vibrating sheet are welded fixedly along the entire circumference of the through hole by means of manual argon arc welding.

The U.S. Pat. No. 6,415,668 B1 published on Jul. 9, 2002 also provides a different type of vibrating sheet, as shown in FIG. 9. Such a vibrating sheet is mainly characterized in that the vibrating sheet consists of four parts welded together, two through holes for the passage of the flow tubes are respectively located in two separate half sheets, two connecting sheets connect the two half sheets together after the two flow tubes extend trough said two half sheets. Such a vibrating sheet is mainly adapted for the circumstance where the two flow tubes cannot extend through the two through holes in the vibrating sheet simultaneously. Thus, one through hole is arranged on each of the two separate half sheets, and then connected the two separate half sheets after the flow tubes extend through the half sheets. In this patent, each half sheet is fixedly welded to the flow tube along the entire circumference of the through hole.

No matter which vibrating sheet in the prior art, they all have a planar structure (namely, the welds formed and the main connecting portion of the vibrating sheet are substantially in the same plane or parallel planes) generally, and the prior art vibrating sheet and the flow tube are finally fixed by means of welding along the entire circumference of the through hole because those skilled in the art all believe that welding of the vibrating sheet and the flow tube along the entire circumference of the through hole can ensure a better connection strength.

In terms of the selection of the welding technique, the prior art usually adopts fusion welding or brazing to weld the vibrating sheet and the flow tube together.

However, for fusion welding such as argon arc welding, plasma welding or laser welding, the flow tube must be locally heated to a fusion state for achieving a better welding effect. During cooling and solidification process, metallic grains in the fused section of the flow tube will be rearranged, which may render coarse the grain structure in this section. Thus, the grain structure is very coarse along the entire circumference at the junction between the flow tube and the vibrating sheet, i.e., an annular weld 180 as shown in FIG. 10. The coarse grain structure will reduce the structural strength of the flow tube, which may result in flow tube breakage that often occurs in actual application.

Furthermore, the requisite local heating in the fusion welding will generate residual stress, which has a great influence on the precision of flow measurement. Upon welding the vibrating sheet by means of local heating, those skilled in the art can all appreciate that the residual stress will be generated in the weld region due to uneven heating of the material. The magnitude and direction of the residual stress will keep changing as time and vibration of the flow tube go on. The residual stress and the stress generated by vibration will be superposed. The magnitude and direction of the superposed stress will also change continuously, which will directly lead to inaccurate measurement of phase difference of the flow tube.

In persistent research of the technique for welding the vibrating sheet and the flow tube, those skilled in the art have made attempts for dozens of years, and would like to choose vacuum brazing technique to fix the vibrating sheet and the flow tube in most cases at the present because this technique causes minimum damages to the flow tube. For eliminating impact of the residual stress, many companies at the present tend to use a zinc-copper alloy or a nickel alloy as a brazing material to braze the entire flow tube in a vacuum environment. Since the brazing temperature can only melt the brazing material and is lower than the fusing temperature of the flow tube, there is no adverse influence on the flow tube performance. Uneven heating will never occur upon holistic heating of the flow tube, thereby producing no residual stress.

However, brazing has its own disadvantages. Since the brazing material is expected to have a fusing point different from that of the flow tube and the vibrating sheet, the brazing material must be different from that of the latter. Additionally, the brazing material often has hardness lower than that of the flow tube and the vibrating sheet, so the location of the brazing material is a weak part of the entire structure. With vibration of the flow tube, the brazing material is pressed and stretched constantly and will creep slowly, and the vibration state of the flow tube will also change gradually, thereby influencing the performance of flow measurement.

Moreover, the other main problem of brazing is that it must be conducted in a vacuum environment, and the weld should be void of bubbles and impurities. Once the weld has bubbles therein, the compressibility of the brazing material will be increased due to low hardness thereof. The weld will come to a failure very early during stretching and compression. It is very easy to braze a tube of relatively small size in a vacuum environment; however, there are numerous difficulties for a flow meter of larger size for the reason that the size of the vacuum furnace is not suitable for the large-sized flow meter or the vacuum degree cannot meet the requirement of vacuum brazing. As such, there are high requirements set for vacuum brazing, and subsequent rigorous examination is necessary for quality guarantee. Brazing is costly and technically difficult.

SUMMARY OF THE INVENTION

In view of the above various problems in the prior art, one primary object of the present invention is to eliminate stress concentration in the local region of the welded portion of the flow tube and the vibrating sheet, so as to increase sensitivity of the Coriolis mass flow meter and the vibrating tube density meter and prolong the service life thereof.

A further object of the present invention is to further improve the load conditions of the flow tube and the vibrating sheet, reduce maximum stress, and enhance connecting strength of the flow tube and the vibrating sheet, so as to further increase sensitivity of the Coriolis mass flow meter and the vibrating tube density meter and further prolong the service life thereof.

In these regards, the inventor of the present invention conducts a profound load analysis of the connecting structure of the flow tube and the vibrating sheet. For easy depiction, rectangular Cartesian coordinates X-Y-Z are used in the stress analyzing diagrams as shown in FIGS. 11 and 12, wherein X-axis is the vibration direction of the flow tube under excitation, Y-axis is a revolving axis direction of the flow tube, and Z-axis is the longitudinal axis direction of the flow tube. As shown results from the load analysis, the flow tubes 111, 112 under excitation generate the out-of-phase vibration in the X-axis direction. Since the vibrating sheet 150 is fixed between the flow tubes 111, 112, the vibrating sheet 150 is compressed and stretched by the flow tubes 111, 112 in the X-axis direction. The stress distribution 401 of the flow tubes 111, 112 in the X-axis direction along the Z-axis is shown in FIG. 11. Since the flow tubes 111, 112 do not vibrate in the Y-axis direction, the vibrating sheet 150 receives no force and does not deform in the Y-axis direction. The stress on the flow tubes 111, 112 in the Y-axis direction along Z-axis is null, and the positions bearing the largest stress are mainly located at the junction of the flow tube and the vibrating sheet in the X-axis direction. In particular, in the present application, the region of the circumferential wall of the flow tube which has an angle of less than 45 degrees with respect to the X-axis direction (namely, a 90 degree arcuate region with the X-axis direction as a central axis) is called as "stress sensitive region" on the flow tube. The corresponding region of the vibrating sheet intersecting with the "stress sensitive region" of the flow tube is called "stress sensitive region" of the vibrating sheet, as denoted by the reference sign 402 in FIG. 12, wherein the junction of the plane formed of X-axis and Z-axis and the flow tube has the maximum stress. The stress sensitive region 402 is the weakest part of the entire flow tube and vibrating sheet connecting structure. On the contrary, in the present application, the region of the circumferential wall of the flow tube which has an angle of not more than 45 degrees with respect to the Y-axis direction (namely, a 90 degree arcuate region with the Y-axis direction as a central axis) is called as "stress insensitive region" on the flow tube. The corresponding region of the vibrating sheet intersecting with the "stress insensitive region" of the flow tube is called "stress insensitive region" of the vibrating sheet, as denoted by the reference sign 420 in FIG. 12, wherein the junction of the plane formed of Y-axis and Z-axis and the flow tube has the minimum stress.

Hereto, those skilled in the art can know that as to the prior art connection that an annular weld is formed along the entire circumference, the stress sensitive region is the part of the flow tube and vibrating sheet connecting structure where connection failure mostly occurs. Especially for the conventional planar flow tube and vibrating sheet connecting structure connected by a process such as a manual argon arc welding as shown in FIG. 10, since there is residual stress along the entire circumference of the annular weld 180, the residual stress in the stress sensitive region and the bending stress resulting from the flow tube vibration can be superposed, the superposed stress in the stress sensitive region may be greater than the allowable stress, and the flow tube may be broken in the stress sensitive region upon vibration.

Based on the above analysis, the inventor of the present application firstly realizes inventively that due to the existence of the stress sensitive region, through holes in the vibrating sheet and welding with the flow tube along the entire circumference of the through hole are disadvantageous to the strength of the flow tube and vibrating sheet connecting structure. An advantageous measure is to avoid welds in the stress sensitive region as much as possible.

Moreover, the inventor of the present application also realizes inventively that more preferably, the vibrating sheet can be designed to have a spatial structure, i.e., the direction of weld and the connecting body of the vibrating sheet are not in the parallel planes, to thereby effectively increase the weld length and enhance the strength of the flow tube and vibrating sheet connecting structure on the basis of ensuring that welded portions are not in the stress insensitive region.

To be specific, in one aspect, the present invention provides a vibrating sheet for use in a Coriolis mass flow meter or a vibrating tube density meter, the vibrating sheet having at least one welded connecting portion that is fixedly welded to the flow tube of the Coriolis mass flow meter or the vibrating tube density meter, the flow tube being excited to vibrate around a revolving axis at the welded junction of the vibrating sheet and the flow tube. In particular, the welded connecting portion is only formed in a stress insensitive region of the vibrating sheet, wherein the stress insensitive region of the vibrating sheet is the region of the vibrating sheet which has an angle of not more than 45 degrees with respect to the revolving axis.

Preferably, the vibrating sheet has a U-shaped or L-shaped structure, at least one slot through which the flow tube partially extends is disposed at the adjoining portion of the sidewalls and the bottom web of the U-shaped or L-shaped structure, two opposite lateral edges of each of the slots are at least partially formed into the welded connecting portions that are fixedly welded to opposite radial sides of the flow tube.

Preferably, the vibrating sheet has a U-shaped structure, the top edges of the two sidewalls of the U-shaped structure are formed into welded portions that are respectively welded to both of the flow tubes.

Preferably, the vibrating sheet has the bottom web that is arranged to provide elastic deformation to reduce stress.

Preferably, the bottom web has a curve in the middle portion thereof; or the bottom web is a curved plate with a curvature.

Preferably, the welded connecting portions of the vibrating sheet are fixedly welded to the stress insensitive region of the flow tube, wherein the stress insensitive region of the flow tube is the region of the circumferential wall of the flow tube which has an angle of not more than 45 degrees with respect to the revolving axis.

Preferably, the stress insensitive region of the vibrating sheet is the region of the vibrating sheet which has an angle of not more than 5 degrees with respect to the revolving axis, and the stress insensitive region of the flow tube is the region of the circumferential wall of the flow tube which has an angle of not more than 5 degrees with respect to the revolving axis.

Preferably, the welded connecting portion extends along the axial direction of the flow tube.

Preferably, the vibrating sheet is a one-piece integrally formed structure.

On one hand, the present invention also provides a Coriolis mass flow meter including any vibrating sheet according to the present invention.

On the other hand, the present invention also provides a vibrating tube density meter including any vibrating sheet according to the present invention.

One main advantage of the present invention is to increase the service life of the Coriolis mass flow meter and the vibrating tube density meter, especially compared with the vibrating sheet and the flow tube welded by a process such as a manual argon arc welding. The vibrating sheet of the present invention is only welded in the stress insensitive region, so the welding residual stress in this region would not be superposed by the bending stress generated by the flow tube vibration. The total stress of the stress sensitive region is less than the allowable stress of the flow tube, and the flow tube will never be broken. Thus, the service life of the Coriolis mass flow meter and the vibrating tube density meter is significantly improved.

The other main advantage of the present invention is to greatly simplify the process, especially for a vacuum brazing process used for welding the vibrating sheet and the flow tube. The vibrating sheet of the present invention mainly overcomes two shortcomings of the above process. One is long time consumption and too much energy waste. The vacuum brazing process usually involves placing the vibrating sheet at a reasonable position of the flow tube, putting a brazing material and a brazing agent at a position to be welded, and then placing the flow tube and the vibrating sheet wholly into the vacuum brazing furnace to be heated to a particular temperature (which usually ranges from 700° C. to 900° C.) at which the brazing material melts but the flow tube and the vibrating sheet do not melt, cooling after a period of time of heat insulation, solidifying the brazing material to secure the vibrating sheet and the flow tube together. The whole process takes about a dozen of hours. The weld of the vibrating sheet of the present invention is in the stress insensitive region, and the stress generated by the local heating has no influence on the performance of the Coriolis mass flow meter and the vibrating tube density meter, so the welding means such as a manual argon arc welding can be used. And, it only takes a few minutes to finish the above procedure by the manual argon arc welding. The other problem of the vacuum brazing is the difficulty in ensuring good quality. Since the brazing material has hardness less than that of the flow tube and the vibrating sheet, the brazing material tends to be subjected to micro-deformation when the flow tube is vibrating. When there are no bubbles in the brazing material, such a micro-deformation can resume, and when there are bubbles in the brazing material, the deformed brazing material will gradually fill in the bubbles, and the deformation thereof cannot resume. The brazing material will be deformed permanently. The permanent deformation changes the position of the supporting points of the vibrating flow tube, and severely influences the performance of the Coriolis mass flow meter and the vibrating tube density meter. Due to manufacturing technical limitations, the vacuum furnace could not generate absolute vacuum. Thus, the vacuum brazing often produces bubbles, and strict examination shall be conducted thereafter to discard the components with bubbles therein. The fixing position of the new vibrating sheet is located in the stress insensitive region, and the stress and displacement in this region are null. Thus, no matter there are bubbles or not in the weld, the performance of the Coriolis mass flow meter and the vibrating tube density meter will never be influenced.

In short, the present invention arranges the welded portion of the vibrating sheet in the stress insensitive region to thereby make it possible to fix the vibrating sheet with the flow tube by many welding manners such as brazing and fusion welding. This not only simplifies the process, but also improves the measurement precision and service life of the Coriolis mass flow meter and the vibrating tube density meter.

The preferred embodiments of the present invention will be described in detail with reference to the following drawings, such that those skilled in the art will have a better understanding of the above-mentioned and other objects, advantages and features of the present invention.

BRIEF DESCRIPTION OF THE DRAWINGS

Preferred embodiments of the present invention will be described in detail with reference to the drawings in an exemplary, but not limitative manner. The same reference signs in the drawings refer to identical or similar components or parts; however, these drawings are not necessarily drawn to scale, wherein.

DETAILED DESCRIPTION OF THE PREFERRED EMBODIMENTS

Figure 1:
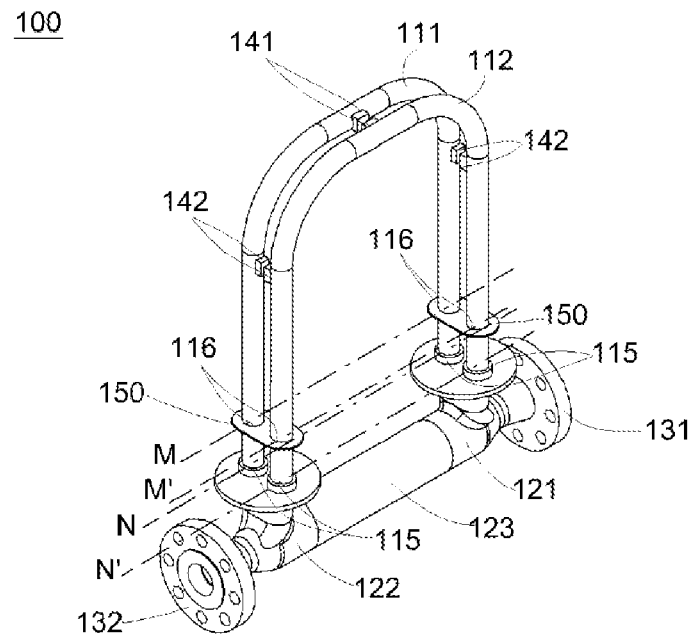
FIG. 1 is a schematic perspective view of a prior art dual-flow-tube Coriolis mass flow meter or vibrating tube density meter.
Figure 2:
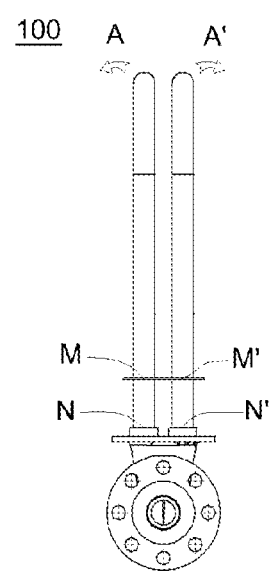
FIG. 2 is a drawing schematically showing the out-of-phase vibration of the flow tube of the prior art dual-flow-tube Coriolis mass flow meter or vibrating tube density meter.
Figure 3:
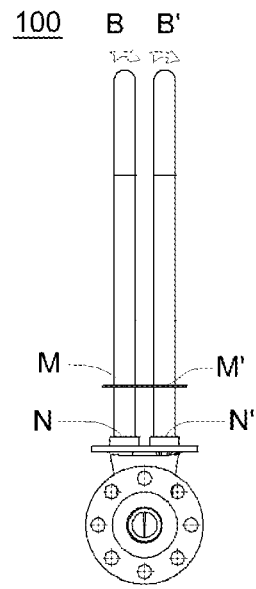
FIG. 3 is a drawing schematically showing the in-phase vibration of the flow tube of the prior art dual-flow-tube Coriolis mass flow meter or vibrating tube density meter.
Figure 4:
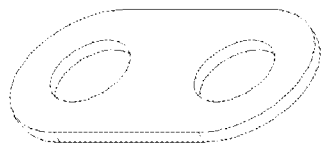
FIG. 4 schematically shows a vibrating sheet for use in the prior art dual-flow-tube Coriolis mass flow meter or vibrating tube density meter.
Figure 5:
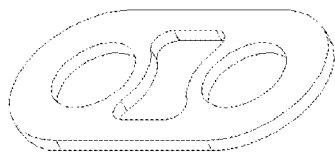
FIG. 5 schematically shows a further vibrating sheet for use in the prior art dual-flow-tube Coriolis mass flow meter or vibrating tube density meter.
Figure 6:
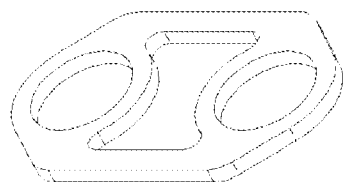
FIG. 6 schematically shows another further vibrating sheet for use in the prior art dual-flow-tube Coriolis mass flow meter or vibrating tube density meter.
Figure 7:
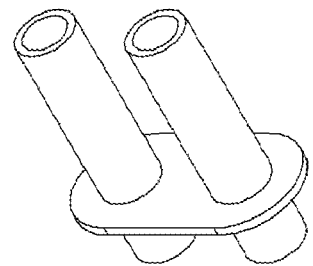
FIG. 7 is a schematic perspective view of the prior art vibrating sheet fixedly welded to the flow tube along the entire circumference of a through hole.
Figure 8:
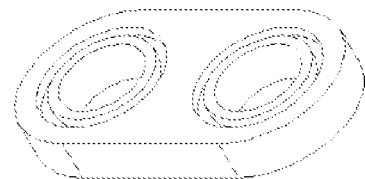
FIG. 8 schematically shows another further vibrating sheet for use in the prior art dual-flow-tube Coriolis mass flow meter or vibrating tube density meter.
Figure 9:
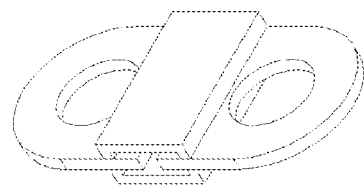
FIG. 9 schematically shows an additional further vibrating sheet for use in the prior art dual-flow-tube Coriolis mass flow meter or vibrating tube density meter.
Figure 10:
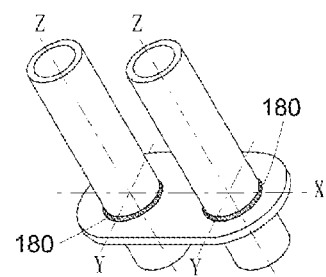
FIG. 10 schematically shows a coarse grain structure formed along the entire circumference at the junction of the flow tube and the vibrating sheet by the fusion welding in the prior art.
Figure 11:
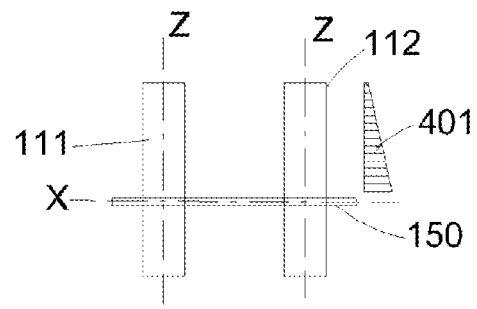
FIG. 11 schematically shows a stress analysis view of a flow tube and vibrating sheet connecting structure analyzed in the present invention.
Figure 12:
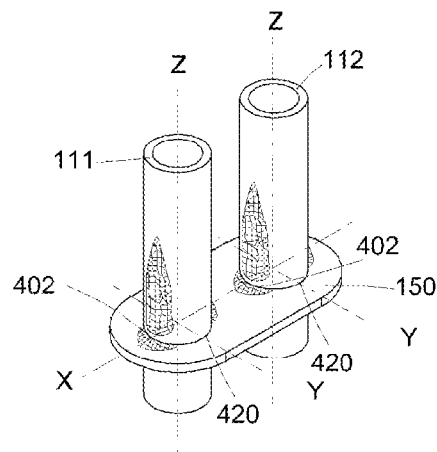
FIG. 12 is a schematic perspective view of a stress analysis result of the flow tube and vibrating sheet connecting structure according to the present invention.
Figure 13:
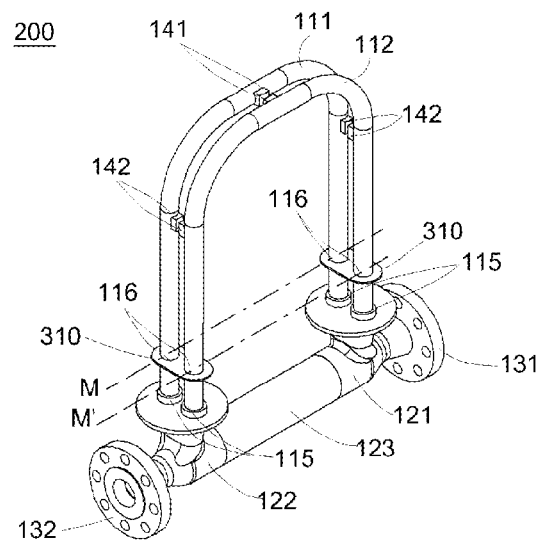
FIG. 13 is a schematic perspective view of a dual-flow-tube Coriolis mass flow meter or a dual-flow-tube vibrating tube density meter according to one preferred embodiment of the present invention.

FIG. 13 is a schematic perspective view of a dual-flow-tube Coriolis mass flow meter or a dual-flow-tube vibrating tube density meter 200 according to one preferred embodiment of the present invention. The entire structure of the Coriolis mass flow meter or the vibrating tube density meter 200 is similar to that of the prior art as shown in FIG. 1. The vibrating sheet 310 also has at least one welded connecting portion that is fixedly welded to the flow tubes 111, 112. The flow tubes 111, 112 are also excited to vibrate around the revolving axes M and M' at the welded junction of the vibrating sheet 310 and the flow tube. However, in the Coriolis mass flow meter or the vibrating tube density meter 200 of the present invention, the welded connecting portion of the vibrating sheet 310 is only formed in a stress insensitive region of the vibrating sheet. In this embodiment, the stress insensitive region of the vibrating sheet 310 is the region of the circumference of the through hole for the passage of the flow tube in the vibrating sheet 310 which has an angle of not more than 45 degrees with respect to the revolving axis. Preferably, the stress sensitive region of the through hole in the vibrating sheet 310 is not in contact with the flow tube wall. For instance, in one embodiment, the through hole in the vibrating sheet 310 may be slightly oval, the region adjacent to the short axis of the oval is a stress insensitive region and forms a welded connecting portion; and the region adjacent to the long axis of the oval is a stress sensitive region, and there is a gap between the stress sensitive region and the flow tube wall. Moreover, in the Coriolis mass flow meter or the vibrating tube density meter 200 of the present invention, a vibration exciter 141 is preferably formed of an exciting coil and a magnet secured in the middle position of the top portion of the flow tube. A vibration sensor 142 preferably formed of a sampling coil and a magnet is mounted on both sides of the vibration exciter 142.

Figure 14:
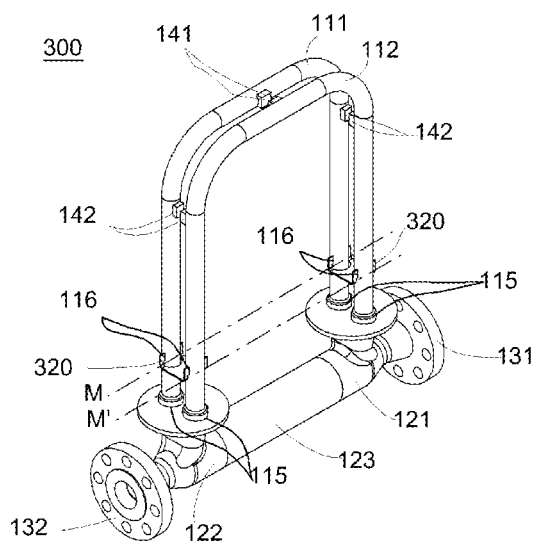
FIG. 14 is a schematic perspective view of a dual-flow-tube Coriolis mass flow meter or a dual-flow-tube vibrating tube density meter according to another preferred embodiment of the present invention.
Figure 15:
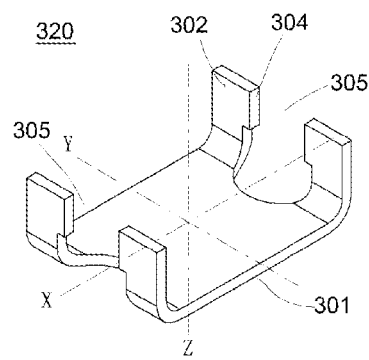
FIG. 15 is a schematic perspective view of a vibrating sheet used for the dual-flow-tube Coriolis mass flow meter or the dual-flow-tube vibrating tube density meter of FIG. 14.
Figure 16:
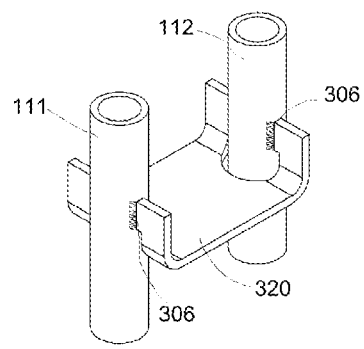
FIG. 16 is a schematic view showing the connection between the vibrating sheet of FIG. 15 and the flow tube of the dual-flow-tube Coriolis mass flow meter or the dual-flow-tube vibrating tube density meter.
Figure 17:
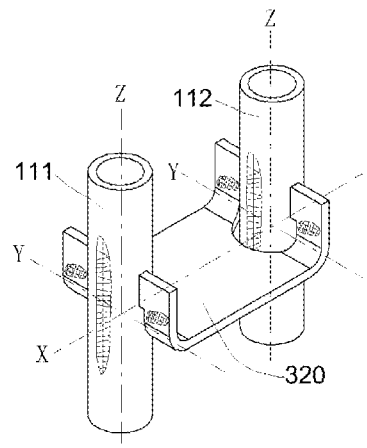
FIG. 17 schematically shows the stress distribution of the vibrating sheet and the flow tube of FIG. 16.

FIG. 14 is a schematic perspective view of a dual-flow-tube Coriolis mass flow meter or a dual-flow-tube vibrating tube density meter 300 according to another preferred embodiment of the present invention, which uses a specially designed vibrating sheet 320 of the present invention. FIG. 15 is a schematic perspective view of the vibrating sheet 320. Preferably, the vibrating sheet 320 is configured into a substantially U-shaped structure. A slot 305 through which the flow tube partially extends is disposed at the adjoining portion of two sidewalls 302 and the bottom web 301 of the U-shaped structure, two opposite lateral edges of each slot are at least partially formed into two welded connecting portions 304 that are fixedly welded to opposite radial sides of the flow tube. FIG. 16 is a schematic view showing the connection between the vibrating sheet of FIG. 15 and the flow tube of the dual-flow-tube Coriolis mass flow meter or the dual-flow-tube vibrating tube density meter, wherein the welds 306 formed between the vibrating sheet 320 and the flow tubes 111, 112 are parallel to the axial direction of the flow tubes. FIG. 17 schematically shows the stress distribution of the vibrating sheet and the flow tube of FIG. 16. As clearly shown in FIG. 17, the welds formed between the vibrating sheet 320 and the flow tubes 111, 112 are located in the stress insensitive region of the vibrating sheet and the flow tubes, and there are no welds in the stress sensitive region.

Figure 18:
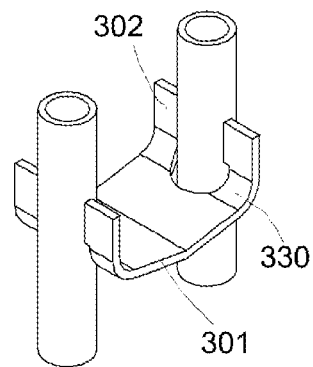
FIG. 18 is a schematic view showing the connection between the vibrating sheet and the flow tube in the dual-flow-tube Coriolis mass flow meter or the dual-flow-tube vibrating tube density meter according to another further preferred embodiment of the present invention.
Figure 19:
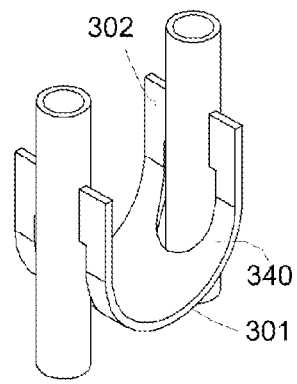
FIG. 19 is a schematic view showing the connection between the vibrating sheet and the flow tube in the dual-flow-tube Coriolis mass flow meter or the dual-flow-tube vibrating tube density meter according to another further preferred embodiment of the present invention.

FIGS. 18 and 19 show two vibrating sheets 330, 340 for use in the dual-flow-tube Coriolis mass flow meter or the dual-flow-tube vibrating tube density meter according to another further preferred embodiment of the present invention. The bottom webs of the vibrating sheets 330, 340 are both configured to provide elastic deformation to reduce the flow tube stress, wherein the vibrating sheet 330 provides elastic deformation by arranging a curve in the middle portion of the bottom web 301 thereof, and the vibrating sheet 340 provides elastic deformation by configuring the bottom web 301 into a curved plate with a curvature.

Figure 20:
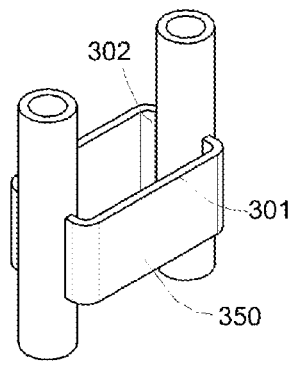
FIG. 20 is a schematic view showing the connection between the vibrating sheet and the flow tube in the dual-flow-tube Coriolis mass flow meter or the dual-flow-tube vibrating tube density meter according to another further preferred embodiment of the present invention.

FIG. 20 is a schematic view showing the connection between the vibrating sheet 350 and the flow tube in the dual-flow-tube Coriolis mass flow meter or the dual-flow-tube vibrating tube density meter according to another further preferred embodiment of the present invention. The vibrating sheet 350 is a U-shaped structure, and the top edges of the sidewalls of the U-shaped structure are formed to be respectively welded to the welded connecting portions of the flow tube. Preferably, two of such vibrating sheets 350 may be used to be fixedly welded to the flow tube from two radial sides of the flow tube respectively.

In the various embodiments of the present invention, the width of the formed weld is preferably the thickness of the vibrating sheet plus about 6 mm to 8 mm. Therefore, for the sake of keeping all welds within the stress insensitive region, it is possible to select a vibrating sheet with a proper thickness according to the factors such as the actual diameter of the flow tube, and a more preferable stress insensitive region can be selected from a larger stress insensitive region, i.e., a 90 degree arcuate region with the revolving axis as a central axis, for instance, the stress insensitive region is more preferably a region of the vibrating sheet which has an angle of not more than 30 or 15 or 10 or 5 or 3 degrees with respect to the revolving axis of the flow tube. The vibrating sheet of the present invention is preferably a one-piece integrally formed structure.

So far, based upon the principle of the present invention, those skilled in the art will appreciate that the present invention may be applied to a single-flow-tube Coriolis mass flow meter and vibrating tube density meter or a multi-flow-tube Coriolis mass flow meter and vibrating tube density meter except the dual-flow-tube Coriolis mass flow meter and vibrating tube density meter.

Figure 21:
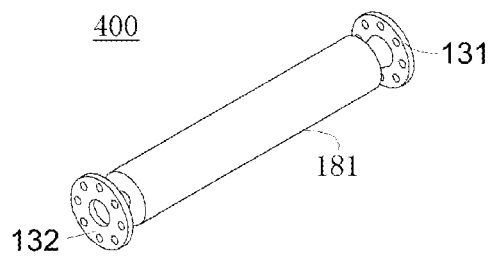
FIG. 21 is a schematic perspective view of a single-flow-tube Coriolis mass flow meter or a single-flow-tube vibrating tube density meter according to another preferred embodiment of the present invention.
Figure 22:
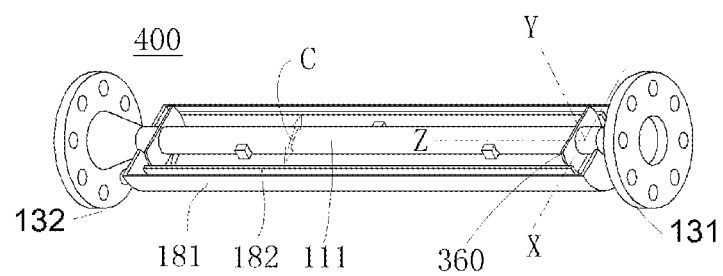
FIG. 22 is a schematic cross-sectional view of the single-flow-tube Coriolis mass flow meter or the single-flow-tube vibrating tube density meter of FIG. 21.
Figure 23:
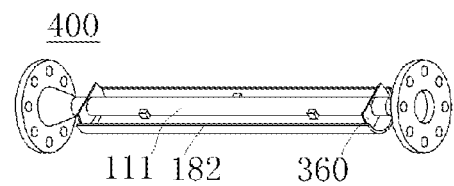
FIG. 23 is a schematic cross-sectional view of the single-flow-tube Coriolis mass flow meter or the single-flow-tube vibrating tube density meter of FIG. 22 after a cover is removed.

FIG. 21 is a schematic perspective view of a single-flow-tube Coriolis mass flow meter or a single-flow-tube vibrating tube density meter 400 according to another preferred embodiment of the present invention. Different from the dual-flow-tube Coriolis mass flow meter or the dual-flow-tube vibrating tube density meter 200, the single-flow-tube Coriolis mass flow meter or the dual-flow-tube vibrating tube density meter 400 does not have manifold blocks 121, 122 and a transverse tube 123, etc. As shown in FIGS. 22 and 23, the single-flow-tube Coriolis mass flow meter or the single-flow-tube vibrating tube density meter 400 usually includes a shield 181, a resonance tube 182 (since there is only one flow tube, a corresponding resonance tube is required), the flow tube 111 and a vibrating sheet 360. The arrow C in FIG. 22 indicates the vibration direction of the flow tube 111. In particular, in the present invention, the welded connecting portion of the vibrating sheet 360 is only formed in the stress insensitive region, that is to say, the welds between the vibrating sheet 360 and the flow tube 111 are only formed in the stress insensitive region.

Figure 24:
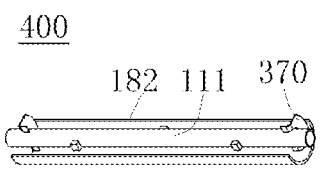
FIG. 24 is a schematic view showing the connection to the vibrating sheet for use in the single-flow-tube Coriolis mass flow meter or the single-flow-tube vibrating tube density meter according to a further preferred embodiment of the present invention.

FIG. 24 is a schematic view showing the connection to the vibrating sheet 370 for use in the single-flow-tube Coriolis mass flow meter or the single-flow-tube vibrating tube density meter according to a further preferred embodiment of the present invention. The vibrating sheet 370 is formed into a substantially L-shaped structure. A slot through which the flow tube 111 partially extends is disposed at the adjoining portion of the sidewall and the bottom web of the L-shaped structure, and two opposite lateral edges of the slot are at least partially formed into the welded connecting portions that are fixedly welded to opposite radial sides of the flow tube 111.

Figure 25:
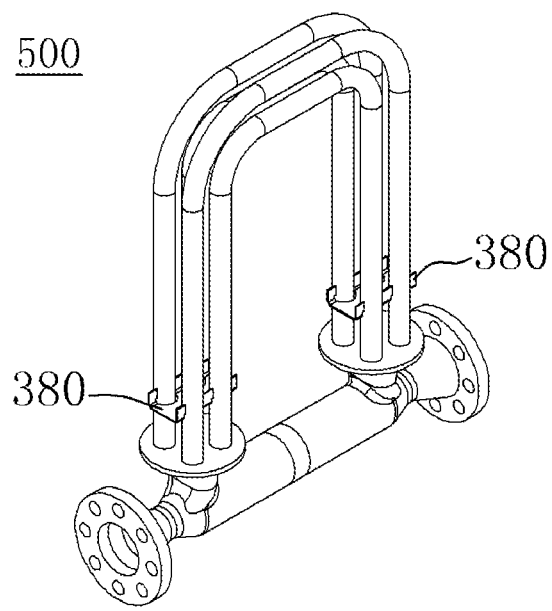
FIG. 25 is a schematic perspective view of the multi-flow-tube Coriolis mass flow meter or the multi-flow-tube vibrating tube density meter according to another preferred embodiment of the present invention.
Figure 26:
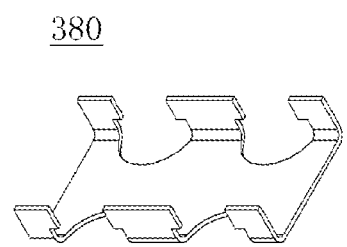
FIG. 26 is a schematic perspective view of a vibrating sheet for use in the multi-flow-tube Coriolis mass flow meter or the multi-flow-tube vibrating tube density meter of FIG. 25 according to another preferred embodiment of the present invention.

FIG. 25 is a schematic perspective view of the multi-flow-tube Coriolis mass flow meter or the multi-flow-tube vibrating tube density meter 500 according to another preferred embodiment of the present invention, wherein there are exemplarily four flow tubes. FIG. 26 is a schematic perspective view of a vibrating sheet 380 for use in the multi-flow-tube Coriolis mass flow meter or the multi-flow-tube vibrating tube density meter 500. Those skilled in the art can all appreciate that such a vibrating sheet 380 for use in the multi-flow-tube Coriolis mass flow meter or the multi-flow-tube vibrating tube density meter 500 is much similar to the above-mentioned vibrating sheets 320, 330, 340 in terms of the holistic structure, but two or more slots should be arranged in each sidewall. This is readily conceivable by those skilled in the art according to the previous disclosure and will not be repeated herein.

Even though several exemplary preferred embodiments are shown and described, those skilled in the art can realize that many other variations or modifications in compliance with these embodiments can be directly determined or derived according to the disclosure of the present application without departing from the spirit and scope of the present invention. Hence, the scope of the present invention shall be understood as covering all other variations or modifications.

The invention claimed is:

1. A vibrating sheet for use in a Coriolis mass flow meter or a vibrating tube density meter, the vibrating sheet having at least one welded connecting portion that is fixedly welded to the flow tube of the Coriolis mass flow meter or the vibrating tube density meter, the flow tube being excited to vibrate around a revolving axis at the welded junction of the vibrating sheet and the flow tube, characterized in that:

the welded connecting portion is only formed in a stress insensitive region of the vibrating sheet, wherein the stress insensitive region of the vibrating sheet is the region of the vibrating sheet which has an angle of not more than 45 degrees with respect to the revolving axis.

2. The vibrating sheet according to claim 1, characterized in that:

the vibrating sheet has a U-shaped or L-shaped structure, at least one slot through which the flow tube partially extends is disposed at sidewalls of the U-shaped or L-shaped structure, and two opposite lateral edges of each of the slots are at least partially formed into two the welded connecting portions that are fixedly welded to opposite radial sides of the flow tube.

3. The vibrating sheet according to claim 1, characterized in that:

the vibrating sheet is a U-shaped structure, and the top edges of the two sidewalls of the U-shaped structure are formed into two the welded connecting portions that are respectively welded to both of the flow tubes.

4. The vibrating sheet according to claim 2, characterized in that:

the vibrating sheet comprises a bottom web, which is arranged to provide elastic deformation to reduce stress.

5. The vibrating sheet according to claim 4, characterized in that:

the bottom web has a curve in the middle portion thereof; or the bottom web is a curved plate with a curvature.

6. The vibrating sheet according to claim 1, characterized in that:

the welded connecting portions of the vibrating sheet are fixedly welded to the stress insensitive region of the flow tube, wherein the stress insensitive region of the flow tube is the region of the circumferential wall of the flow tube which has an angle of not more than 45 degrees with respect to the revolving axis.

7. The vibrating sheet according to claim 6, characterized in that:

the stress insensitive region of the vibrating sheet is the region of the vibrating sheet which has an angle of not more than 5 degrees with respect to the revolving axis, and the stress insensitive region of the flow tube is the region of the circumferential wall of the flow tube which has an angle of not more than 5 degrees with respect to the revolving axis.

8. The vibrating sheet according to claim 1, characterized in that:
   the welded connecting portion extends along the axial direction of the flow tube.

9. The vibrating sheet according to claim 1, characterized in that:
   the vibrating sheet is a one-piece integrally formed structure.

10. A Coriolis mass flow meter including the vibrating sheet according to claim 1.

11. A vibrating tube density meter including the vibrating sheet according to claim 1.

12. The vibrating sheet according to claim 3, characterized in that:
   the vibrating sheet comprises a bottom web, which is arranged to provide elastic deformation to reduce stress.

\* \* \* \* \*